United States Patent [19]

Aya et al.

[11] Patent Number: 4,530,717
[45] Date of Patent: Jul. 23, 1985

[54] SYNERGISTIC HERBICIDAL MIXTURES OF SUBSTITUTED PHENYLSULFONYLUREA DERIVATIVES AND BENZTHIAZOL-2-YL-OXYACETIC ACID N-METHYLANILIDE

[75] Inventors: Masahiro Aya; Kazuomi Yasui; Atsumi Kamochi, all of Tokyo, Japan

[73] Assignee: Nihon Tokushu Noyaku Seizo K.K., Tokyo, Japan

[21] Appl. No.: 459,011

[22] Filed: Jan. 18, 1983

[30] Foreign Application Priority Data

Jan. 22, 1982 [JP] Japan .................. 57-7453

[51] Int. Cl.³ ................. A01N 43/02; A01N 43/66
[52] U.S. Cl. ......................... 71/90; 71/92; 71/93
[58] Field of Search ..................... 71/90, 93

[56] References Cited

U.S. PATENT DOCUMENTS 4,336,057 6/1982 Bieringer et al. ............ 71/90
4,378,991 4/1983 Levitt .......................... 71/93

FOREIGN PATENT DOCUMENTS 0005501 11/1979 European Pat. Off. ........ 71/90
0044211 1/1982 European Pat. Off. ........ 71/93

OTHER PUBLICATIONS

Nihon, "Herbicidal Agents,"(1980).
Res. Discl.—CA 93, No. 63465w, (1980).
Index—Chemical Name, (1976).
Weed Sci.—Cover page—vol. 24, No. 6, (1976).

*Primary Examiner*—Glennon H. Hollrah
*Assistant Examiner*—Andrew Duff Meikle
*Attorney, Agent, or Firm*—Sprung Horn Kramer & Woods

[57] ABSTRACT

A herbicidal synergistic compound combination containing as active ingredients
(1) a compound selected from substituted phenylsulfonylurea derivatives of the general formula

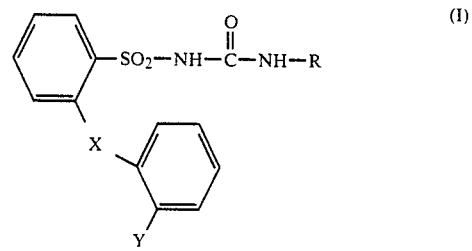

in which
X represents an oxygen atom or a direct bond,
Y represents a hydrogen or chlorine atom, and
R represents a group of the general formula

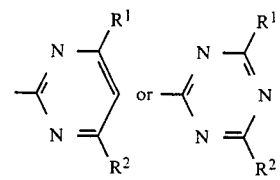

in which $R^1$ and $R^2$ each independently represents a methyl group or a methoxy group, and
(2) benzthiazol-2-yl-oxyacetic acid N-methylanilide of the formula

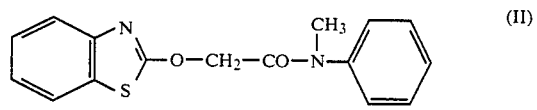

alone or in admixture with a solid or liquid diluent or carrier, is effective for controlling perennial weeds, especially paddy field weeds.

7 Claims, No Drawings

SYNERGISTIC HERBICIDAL MIXTURES OF SUBSTITUTED PHENYLSULFONYLUREA DERIVATIVES AND BENZTHIAZOL-2-YL-OXYACETIC ACID N-METHYLANILIDE

The present invention relates to new herbicidal synergistic combinations of certain substituted phenylsulfonylurea derivatives and benzthiazol-2-yloxyacetic acid N-methylanilide.

It is already known that substituted phenylsulfonylurea derivatives of the formula (I) herein below have herbicidal action (Japanese Patent Application Nos.Sho56-8977 and No. Sho56-144590), corresponding to U.S. application Ser. No. 340,903, filed Jan. 20, 1982 and Ser. No. 415,629, filed Sept. 7, 1982 respectively, the both are now pending.

It is also known that benzthiazol-2-yloxyacetic acid N-methylanilide has herbicidal action (Japanese Laid-open Patent Application No.Sho 54-154762).

However, for example, in the case of paddy field weeds, there are many herbicides effective on annual weeds but there is almost no herbicide effective to control perennial weeds. Since perennial weeds generally grow actively and their breeding period is long, their complete control is difficult. Therefore herbicides are needed which have a wide weed killing spectrum so as to kill a wide variety of weeds.

Further, recent paddy field cultivation has provided weeds with more opportunity to grow than ever before because the introduction of mechanical cultivation and the earlier transplantation technique have spread weeds widely, so that their complete control could not be expected merely by single applications of a herbicide.

Thus there has been a need to develop herbicides which can completely control all weeds present by a single application, which have a high degree of safety to paddy field rice.

The present invention now provides a herbicidal composition containing as active ingredient:

(1) a substituted phenylsulfonylurea derivative of the general formula

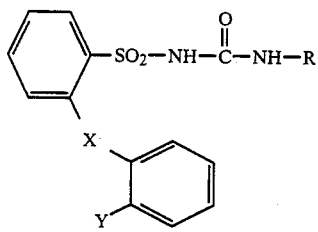

in which
X represents an oxygen atom or a direct bond,
Y represents a hydrogen or a chlorine atom, and
R represents a group of the general formula

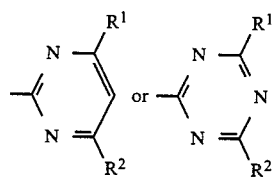

in which $R^1$ and $R^2$ each independently represents a methyl group or a methoxy group, and (2) benzthiazol-2-yloxyacetic acid N-methylanilide of the formula

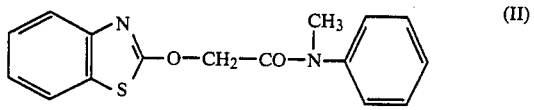

alone or in admixture with a solid or liquid diluent or carrier.

Surprisingly, the herbicidal action of the active compound combinations according to the invention is considerably higher than the actions of the individual components or the sum of the actions of the individual components. In particular, the combination according to the present invention has a particularly good synergistic effect and potentiating effect even at a concentration where each active ingredient, if used singly, would not have a satisfactory action. The synergistic combinations show accurate and selective weed control, for example, they exhibit a remarkable control effect against weeds in advanced stages of growth (e.g. weeds in the stage corresponding to the four-leaf stage of *Echinochloa crus-galli* Beauv. var.) by their synergistic effect, and at the same time, they can achieve satisfactory selective control against those kinds of weeds on which the single chemicals could not exhibit a satisfactory effect and thus they display a wide weed killing spectrum (e.g. against weeds such as *Eleocharis kuroguwai* Ohwi, *Sagittaria trifolia* L., *Scirpus etuberulatus*, *Scirpus lineolatus* Franch et Sav. and *Scirpus planiculmis* Fr Schmidt). Further the active compound combinations of the present invention show a good residual effect. The present invention thus represents a significant contribution to the art.

Examples of particularly preferred active ingredients of formula (I) of component (1) include the following compounds:

Compound No. (1)
N-2-Biphenylylsulfonyl, N'-(4-methoxy-6-methylpyrimidin-2-yl)urea; m.p. 199° to 202° C.;

Compound No. (2)
N-2-Biphenylsulfonyl, N'-(4,6-dimethyl-pyrimidin-2-yl)urea; m.p. 203° to 208° C.;

Compound No. (3)
N-2-Phenoxyphenylsulfonyl, N'-(4-methoxy-6-methylpyrimidin-2-yl)urea; m.p. 196° to 200° C.;

Compound No. (4)
N-2-(2-Chlorophenoxy)phenylsulfonyl, N'-(4-methoxy-6-methyl-pyrimidin-2-yl)urea; m.p. 216° to 220° C.;

Compound No. (5)
N-2-Phenoxyphenylsulfonyl, N'-(4,6-dimethylpyrimidin-2-yl)urea; m.p. 178° to 180° C.;

Compound No. (6)
N-2-Biphenylylsulfonyl, N'-(4-methoxy-6-methyl-1,3,5-triazin-2-yl)urea; m.p. 190° to 193° C.;

Compound No. (7)
N-2-Biphenylylsulfonyl, N'-(4,6-dimethoxy-1,3,5-triazin-2-yl)urea; m.p. 175° to 180° C.;

Compound No. (8)
N-2-Phenoxyphenylsulfonyl, N'-(4-methoxy-6-methyl-1,3,5-triazin-2-yl)urea; m.p. 185° to 190° C.; and Compound No. (9)
N-2-Phenoxyphenylsulfonyl, N'-(4,6-dimethoxy-1,3,5-triazin-2-yl)urea; m.p. 160° to 165° C.

The weight ratios of the active compound groups in the active compound combinations can vary within relatively wide limits. In general the active compound of formula (I) and the active compound of formula (II) are present in a ratio by weight of 1:10 to 1:1, preferably 1:5 to 1:1. Since the herbicidal combinations according to the present invention have a good selectivity with regard to cultivated plants, i.e. they show no phytotoxicity at concentrations commonly employed, they can be favorably used as herbicides for weed control. By "weeds" in the broadest sense there are meant plants growing in places where they are not desired.

Whether the compound combinations according to the invention act as total herbicides or selective herbicides depends essentially on the amount used.

The active compound combinations according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compound combinations according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Iriticum, Hordeum, Avena, Secale, Sorghum, Panicum, Saccharum, Ananas, Asparagus and Allium.

However, the use of the active compound combinations according to the invention is in no way restricted to these genera but also embraces other plants, in the same way.

Depending on the concentrations, the compound combinations can be used for the total combating of weeds, for example on industrial terrain and railway tracks and on paths and squares with or without trees. Equally, the compound combinations can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

It should be pointed out that the combinations according to the invention exhibit a superior selective control effect especially when used as pre-germination soil treating agents and as plant- and soil-treating agents for paddy field weeds.

For example, they have a herbicidal activity against the following paddy field weeds without showing any phytotoxicity to rice plants:

the dicotyledon weeds; *Rotala indica* Koehne, *Lindernia Procumbens* Philcox, *Ludwigia prostrata* Roxburgh, *Potamogeton distinctus* A. Benn, and *Elatine triandra* Schk; and the monocotyledon weeds; *Echinochloa crus-galli* Beauv. var, *Monochoria vaginalis* Presl, *Eleocharis acicularis* L., *Eleocharis kuroguwai* Ohwi, *Cyperus difformis* L., *Cyperus serotinus* Rottboel, *Sagittaria pygmaea* Miq, *Sagittaria trifolia* L., *Alisma canaliculatum* A. Br. et Bouche, *Scirpus juncoides* Roxburgh var., *Scirpus lineolatus* Franch et Sav., *Scirpus etuberulatus,* and *Scirpus planiculmis* Fr., Schmidt.

The active compound combinations can be converted into the customary formulations, such as solutions, emulsions, suspensions, powders, pastes and granules.

These formulations may be produced in known manner, for example by mixing the active compound combinations with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.01 to 95 percent by weight of active compound combinations, preferably from 0.5 to 60 percent by weight.

The active compound combinations according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compound combinations can be used as such, as their formulations or as the use forms prepared therefrom, such as ready-to-use solutions, emulsions, suspensions, powders, pastes and granules. They may be used in the customary manner, for example by spraying, atomizing, dusting, scattering and watering.

It is also possible to apply the active compound combination by means of the ultra-low-volume method, whereby it is possible to employ the compounds at a concentration of up to 100%. The active compounds can also be incorporated into the soil.

In actual use, the content of the active compound combination in the said various formulations or ready-to-use preparations is generally 0.01 to 95% by weight, preferably 0.05 to 60% by weight.

The dosage of the active compound combination per unit area is generally 0.1 to 5 kg, preferably 0.5 to 3 kg, per hectare. In special cases, however, it is possible, or sometimes even necessary to use a dosage out of the range specified above.

The present invention also provides herbicidal compositions containing as active ingredient a compound combination of the present invention in admixture with a solid diluent or carrier or in admixture with a liquid diluent or carrier containing a surface-active agent.

The present invention also provides a method of combating weeds (especially paddy field weeds) which comprises applying to the weeds, or to a habitat thereof, a compound combination of the present invention alone or in the form of a composition containing as active ingredient a compound combination of the present invention in admixture with a diluent or carrier.

The present invention further provides crops protected from damage by weeds by being grown in areas in which immediately prior to and/or during the time of the growing a compound combination of the present invention was applied alone or in admixture with a diluent or carrier.

It will be seen that the usual methods of providing a harvested crop may be improved by the present invention.

The compositions according to the invention and the herbicidal activity of the present compound combinations are illustrated by the following examples. In these examples, the compounds of formula (I) are indicated by a number given in brackets corresponding to the number assigned to the preferred compounds given earlier in the text, and the compound "(II)" is benzthiazol-2-yloxyacetic acid N-methylanilide.

EXAMPLE i

25 Parts of water were added to a mixture of 1 part of compound (3), 5 parts of the compound (II), 29 parts of bentonite (montmorillonite), 63 parts of talc and 2 parts of lignin sulfonate, and the resulting mixture was intimately kneaded and finely divided by means of an extruding pelletizer to give granules of 10 to 40 mesh, which were then dried at 40° to 50° C. The granules obtained were applied by scattering.

EXAMPLE ii

25 Parts of water were added to a mixture of 1.5 parts of compound (7), 3.5 parts of the compound (II), 35 parts of bentonite (montmorillonite), 58 parts of talc and 2 parts of lignin sulfonate, and the resulting mixture was intimately kneaded and finely divided by means of an extruding pelletizer to give granules of 10 to 40 mesh, which were then dried at 40° to 50° C. The granules obtained were applied by scattering.

EXAMPLE iii

98 Parts of clay particles of a size distribution of 0.2 to 2 mm were placed in a rotary mixer and a solution of 1 part of compound (7) and 1 part of the compound (II) in an organic solvent was sprayed over the particles while rotating, thereby wetting the particles uniformly. They were then dried at 40° to 50° C. to form granules. The granules obtained were applied by scattering.

EXAMPLE iv

25 Parts of water were added to a mixture of 4 parts of a compound combination comprising the compound (II) and compound (1), (4), (6) or (9), with 34 parts of bentonite (montmorillonite), 58 parts of talc and 2 parts of lignin sulfonate, and the resulting mixture was intimately kneaded and finely divided by means of an extruding pelletizer to give granules of 10 to 40 mesh, which were then dried at 40° to 50° C. The granules obtained were applied by scattering.

EXAMPLE v

15 Parts of compound (3), 35 parts of the compound (II), 45 parts of a 1:5 mixture of powdered diatomaceous earth and powdered clay, 2 parts of sodium alkylbenzenesulfonate and 3 parts of sodium alkylnaphthalenesulfonateformalin condensate were ground and mixed together to form a wettable powder. It was diluted with water before spraying.

EXAMPLE vi

10 Parts of compound (7), 20 parts of the compound (II), 40 parts of xylene, 15 parts of methyl ethyl ketone, 8 parts of polyoxyethylene alkyl phenyl ether and 7 parts of calcium alkylbenzenesulfonate were mixed by stirring to form an emulsifiable concentrate. It was diluted with water before spraying.

The herbicidal activity of the active compound combination of the invention is illustrated by the following biotest examples.

EXAMPLE A

The granules of Example iv were applied to a paddy field where *Echinochloa crus-galli* Beauv. var was growing in the four-leaf stage at a dosage of 1.8 kg per hectare. The said paddy field weed was successfully exterminated.

EXAMPLE B

Test for Control Effect on Paddy Field Weeds under Full Water Condition

Preparation of Test Composition

Using a pelletizer and a conventional pelletizing method, the following formulation was prepared and formed into cylindrical pellets of 0.5 mm in diameter and 1 to 3 mm in length.

Formulation (100 parts by weight in total)

| Active compounds: | 1 to 5 parts respectively |
|---|---|
| Polyoxyethylene alkyl phenyl ether: | 2.5 parts |
| Bentonite: | 30 parts |
| Talc: | 61.5 to 66.5 parts |

(The amount of talc was varied according to the amount of the active compounds, to give the total 100 parts).

Testing Method

The test field was ploughed to a depth of 20 to 25 cm by the conventional rice cultivating methods, just after which water was introduced from an irrigation channel into the field to a depth of 1 to 2 cm and the first tilling was carried out. One or two days after the first tilling, water was again introduced to a depth of about 5 cm and the last tilling was carried out. Two days after the last tilling, the water depth of the field was adjusted to 2 to 3 cm, rice seedlings grown in a nursery for this purpose (15 days old of leaf age, 2 to 2.5 leaf stage, 15 to 17 cm in height) were transplanted 3 to 5 plants per root, using a rice planting machine. Immediately after the transplantation, the field was partitioned into areas of 20 m² each (2 m × 10 m) using rigid plastic sheets, and seeds of the test weed were inoculated at a rate of 10 to 20 per square meter at a depth of 2 to 3 cm from the ground surface. Thereafter, the water depth was maintained at 3 to 5 cm for a prolonged time. Twenty-five days after the transplantation, the composition as prepared above was applied to water. Four weeks after the chemical treatment, the control effect was investigated according to the following criterion.

The evaluation of the effect is expressed in the following scale 0 to 10 according to the percent weed kill relative to that in the non-treated area:
10: 100% (complete destruction)
9: 90% or more but less than 100%
8: 80% or more but less than 90%
7: 70% or more but less than 80%
6: 60% or more but less than 70%
5: 50% or more but less than 60%
4: 40% or more but less than 50%
3: 30% or more but less than 40%
2: 20% or more but less than 30%
1: 10% or more but less than 20%
0: less than 10%

The rating "0" in the column of the phytotoxicity to rice plants means the absence of phytotoxicity.

The results of the test are shown in Table 1 below.

and scope of the invention will suggest themselves to those skilled in the art.

We claim:

1. A herbicidal composition consisting essentially of a herbicidally effective amount of
   (1) a substituted phenylsulfonylurea derivative of the formula

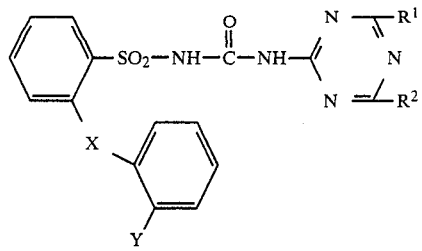

in which
X is an oxygen atom or a direct bond,
Y is a hydrogen or chlorine atom, and
$R^1$ and $R^2$ each independently is a methyl group or a methoxy group, plus
(2) about 1 to 5 times its weight of benzthiazol-2-yloxyacetic acid N-methylanilide of the formula

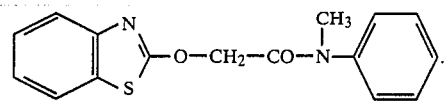

2. A herbicidal composition according to claim 1, wherein (1) is N-2-biphenylylsulfonyl, N'-(4-methoxy-6-methyl-1,3,5-triazin-2-yl)urea.

3. A herbicidal composition according to claim 1, wherein (1) is N-2-biphenylylsulfonyl, N'-(4,6-dimethoxy-1,3,5-triazin-2-yl)urea.

4. A herbicidal composition according to claim 1, wherein (1) is N-2-phenoxyphenylsulfonyl, N'-(4-methoxy-6-methyl-1,3,5-triazin-2-yl)urea.

5. A herbicidal composition according to claim 1, wherein (1) is N-2-phenoxyphenylsulfonyl, N'-(4,6-dimethoxy-1,3,5-triazin-2-yl)urea.

6. A method of combating weeds which comprises applying to the weeds or a habitat thereof a herbicidally effective amount of a composition according to claim 1.

7. The method according to claim 6, wherein (1) is N-2-biphenylylsulfonyl, N'-(4-methoxy-6-methyl-1,3,5-triazin-2-yl)urea,
N-2-biphenylylsulfonyl, N'-(4,6-dimethoxy-1,3,5-triazin-2-yl)urea,
N-2-phenoxyphenylsulfonyl, N'-(4-methoxy-6-methyl-1,3,5-triazin-2-yl)urea or
N-2-phenoxyphenylsulfonyl, N'-(4,6-dimethoxy-1,3,5-triazin-2-yl)urea.

TABLE 1

| Compound Amount of Active Ingredient kg/ha | | Herbicidal Effect Treated 25 Days after Transplantation | | | | | |
|---|---|---|---|---|---|---|---|
| | | Scirpus lineolatus Franch et Sav. | Weeds | | | | Phytotoxicity Rice |
| | | | Scirpus etuberulatus | Eleocharis Kuroguwai Ohwi | Scirpus planiculmis Fr. Schmidt | Sagittaria trifolia L. | |
| Compounds (7) + | (II) | | | | | | |
| 0.3 | 1.5 | 10 | 10 | 10 | 10 | 10 | 0 |
| 0.3 | 0.3 | 10 | 10 | 10 | 10 | 10 | 0 |
| Compounds (3) + | (II) | | | | | | |
| 0.45 | 1.05 | 10 | 10 | 10 | 10 | 10 | 0 |
| Compound (7) | 0.3 | 3 | 3 | 3 | 2 | 3 | 0 |
| Compound (3) | 0.45 | 3 | 3 | 3 | 2 | 3 | 0 |
| Compound (II) | 1.5 | 2 | 2 | 1 | 1 | 0 | 0 |

It will be understood that the specification and examples are illustrative but not limitative of the present invention and that other embodiments within the spirit

* * * * *